United States Patent
Fujii et al.

(10) Patent No.: US 11,369,276 B2
(45) Date of Patent: Jun. 28, 2022

(54) BLOOD PRESSURE MEASUREMENT DEVICE

(71) Applicants: OMRON HEALTHCARE Co., Ltd., Kyoto (JP); OMRON Corporation, Kyoto (JP)

(72) Inventors: Kenji Fujii, Kyoto (JP); Yasuhiro Kawabata, Kyoto (JP); Naomi Matsumura, Kyoto (JP); Reiji Fujita, Kyoto (JP); Akito Ito, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 0 days.

(21) Appl. No.: 17/029,323

(22) Filed: Sep. 23, 2020

(65) Prior Publication Data
US 2021/0000353 A1     Jan. 7, 2021

Related U.S. Application Data

(63) Continuation of application No. PCT/JP2019/011566, filed on Mar. 19, 2019.

(30) Foreign Application Priority Data

Apr. 5, 2018    (JP) .............................. JP2018-072870

(51) Int. Cl.
*A61B 5/021*      (2006.01)
*A61B 5/022*      (2006.01)
(Continued)

(52) U.S. Cl.
CPC ...... *A61B 5/02125* (2013.01); *A61B 5/02141* (2013.01); *A61B 5/02225* (2013.01);
(Continued)

(58) Field of Classification Search
CPC . A61B 5/02125; A61B 5/6824; A61B 5/1116; A61B 2560/0223
See application file for complete search history.

(56) References Cited

U.S. PATENT DOCUMENTS

| | | |
|---|---|---|
| 5,649,543 A | 7/1997 | Hosaka et al. |
| 2007/0055163 A1 | 3/2007 | Asada et al. |

(Continued)

FOREIGN PATENT DOCUMENTS

| | | |
|---|---|---|
| JP | H7 327940 A | 12/1995 |
| JP | 2011-509733 A | 3/2011 |

(Continued)

OTHER PUBLICATIONS

International Search Report of the International Searching Authority for PCT/JP2019/011566 dated Jun. 18, 2019.

(Continued)

*Primary Examiner* — Daniel L Cerioni
*Assistant Examiner* — Raymond P Dulman
(74) *Attorney, Agent, or Firm* — Wenderoth, Lind & Ponack, L.L.P.

(57) ABSTRACT

A blood pressure measurement device according to one aspect includes: a blood pressure measurement unit configured to measure blood pressure at a measurement target site of a measurement target subject; a pulse transit time measurement unit configured to measure a pulse transit time at the measurement target site of the measurement target subject; a blood pressure value calculation unit configured to calculate a blood pressure value, on the basis of measurement results of the pulse transit time and a relational expression representing a correlation between the pulse transit time and the blood pressure; a posture instruction unit configured to instruct the measurement target subject to assume a plurality of postures in which height positions of (Continued)

the measurement target site with respect to a heart of the measurement target subject are different from each other; and a calibration unit configured to calibrate the relational expression, on the basis of the blood pressure measured by the blood pressure measurement unit and the pulse transit time measured by the pulse transit time measurement unit, for each of the plurality of postures.

16 Claims, 13 Drawing Sheets

(51) Int. Cl.
 *A61B 5/11* (2006.01)
 *A61B 5/00* (2006.01)
 *A61B 5/0235* (2006.01)
(52) U.S. Cl.
 CPC .......... *A61B 5/1116* (2013.01); *A61B 5/6824* (2013.01); *A61B 5/0235* (2013.01); *A61B 2560/0223* (2013.01); *A61B 2562/0247* (2013.01)

(56) References Cited

U.S. PATENT DOCUMENTS

| | | | | |
|---|---|---|---|---|
| 2010/0076328 | A1* | 3/2010 | Matsumura | A61B 5/6843 600/500 |
| 2010/0241011 | A1* | 9/2010 | McCombie | A61B 5/021 600/485 |
| 2011/0009718 | A1 | 1/2011 | Gavish | |
| 2013/0018272 | A1 | 1/2013 | Hori | |
| 2015/0327785 | A1 | 11/2015 | Lading et al. | |
| 2017/0332963 | A1 | 11/2017 | Murakami et al. | |
| 2017/0340209 | A1* | 11/2017 | Klaassen | A61B 5/021 |
| 2017/0360306 | A1* | 12/2017 | Narasimhan | A61B 5/02108 |
| 2018/0263518 | A1 | 9/2018 | Shimuta | |
| 2018/0353089 | A1* | 12/2018 | Choi | A61B 5/02416 |
| 2020/0121201 | A1* | 4/2020 | Redtel | A61B 5/02007 |

FOREIGN PATENT DOCUMENTS

| | | |
|---|---|---|
| JP | 5984088 B2 | 9/2016 |
| JP | 2017-521115 A | 8/2017 |
| JP | 2017-209486 A | 11/2017 |
| WO | 2007/024777 A2 | 3/2007 |
| WO | 2011/122253 A1 | 10/2011 |
| WO | 2017/086071 A1 | 5/2017 |

OTHER PUBLICATIONS

English translation of International Search Report of the International Searching Authority for PCT/JP2019/011566 dated Jun. 18, 2019.

International Preliminary Report on Patentability (Chapter II) of the International Preliminary Examining Authority for PCT/JP2019/011566 dated Oct. 21, 2019.

English translation of the International Preliminary Report on Patentability dated Oct. 8, 2020 in International (PCT) Application No. PCT/JP2019/011566.

* cited by examiner

[Fig. 1]
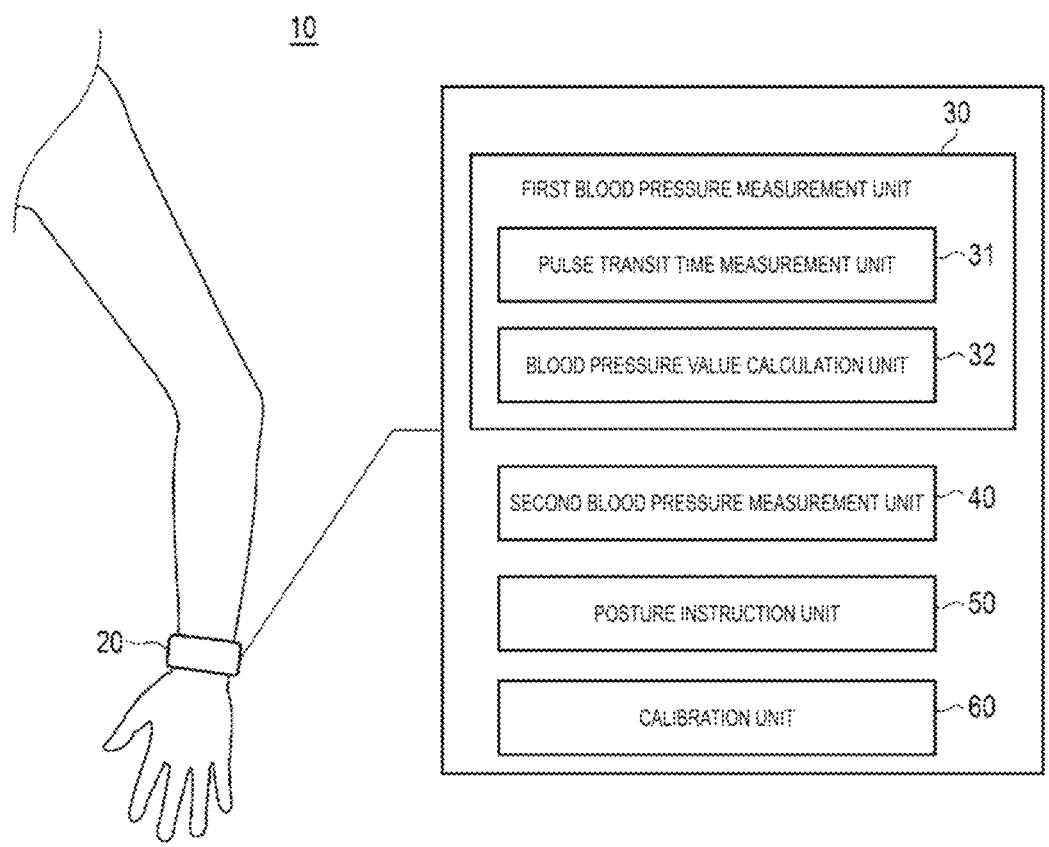

[Fig. 2]
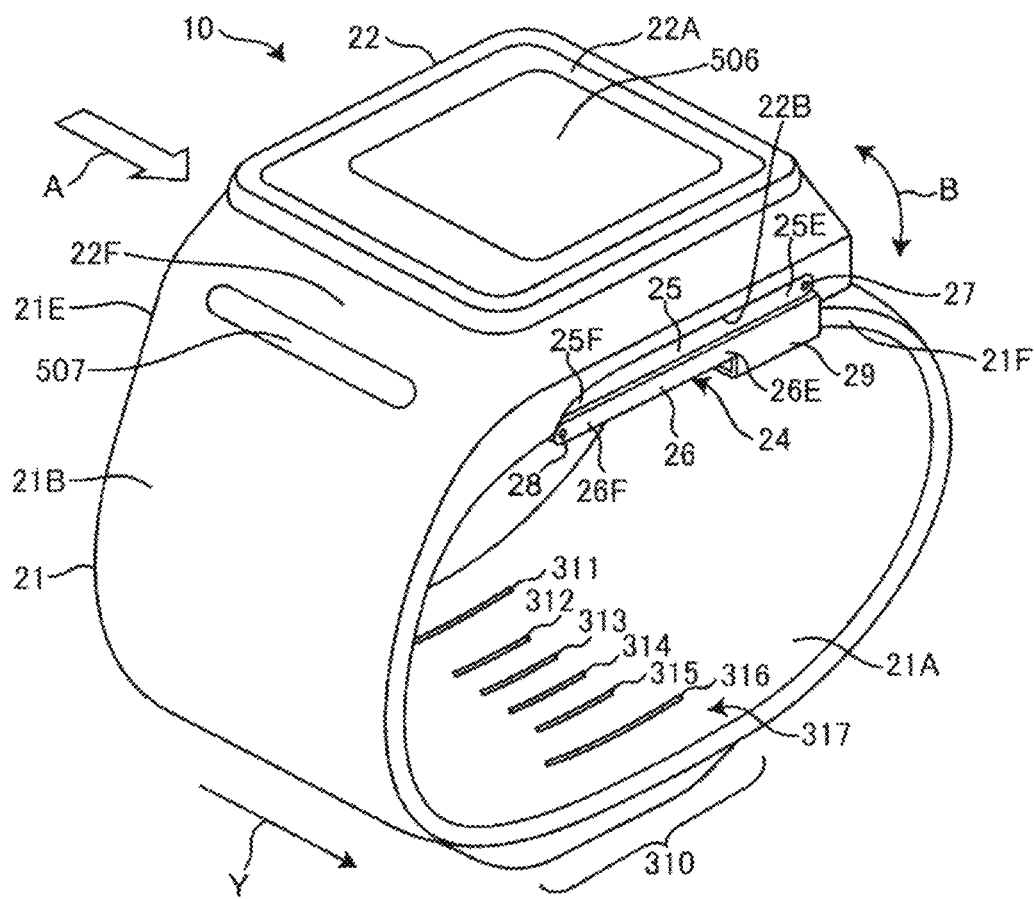

[Fig. 3]
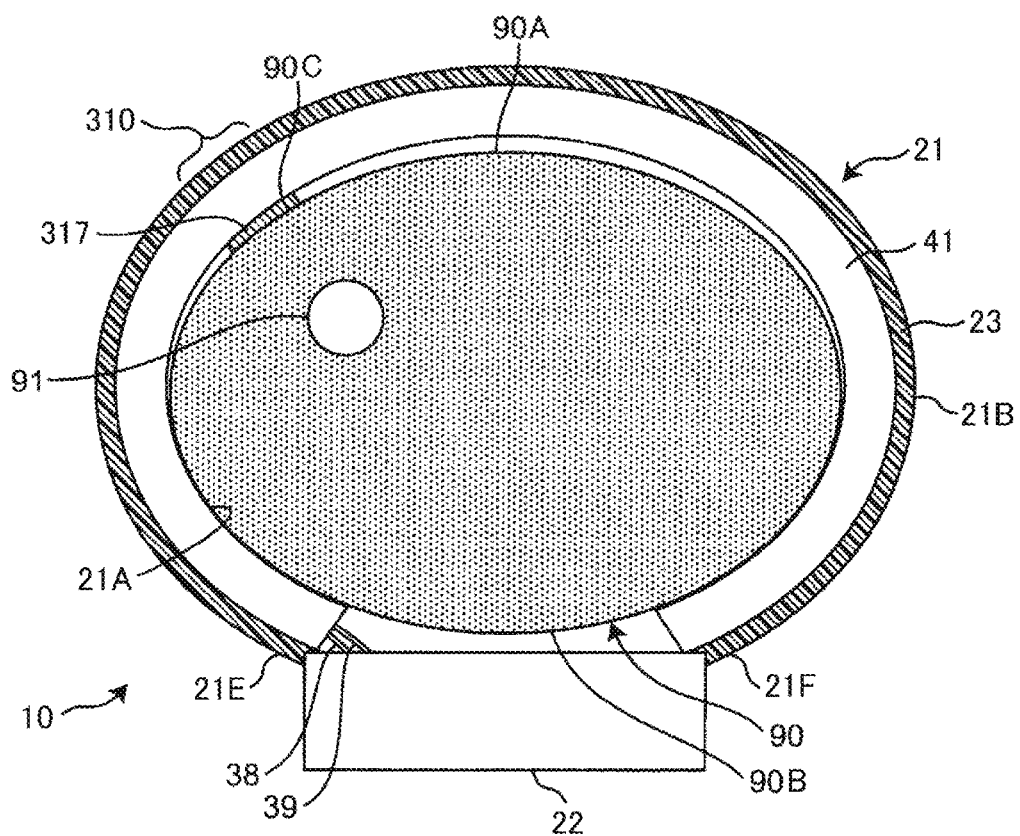

[Fig. 4]
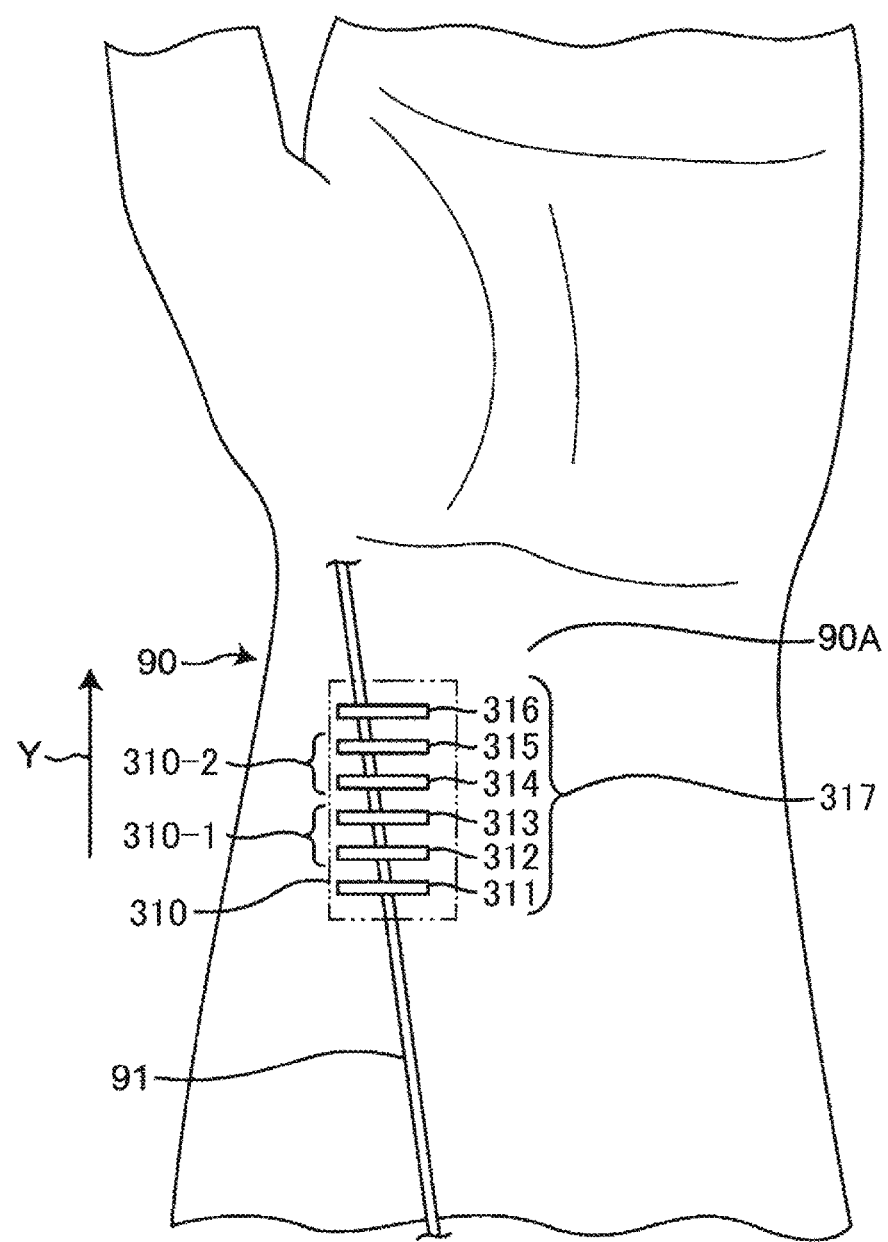

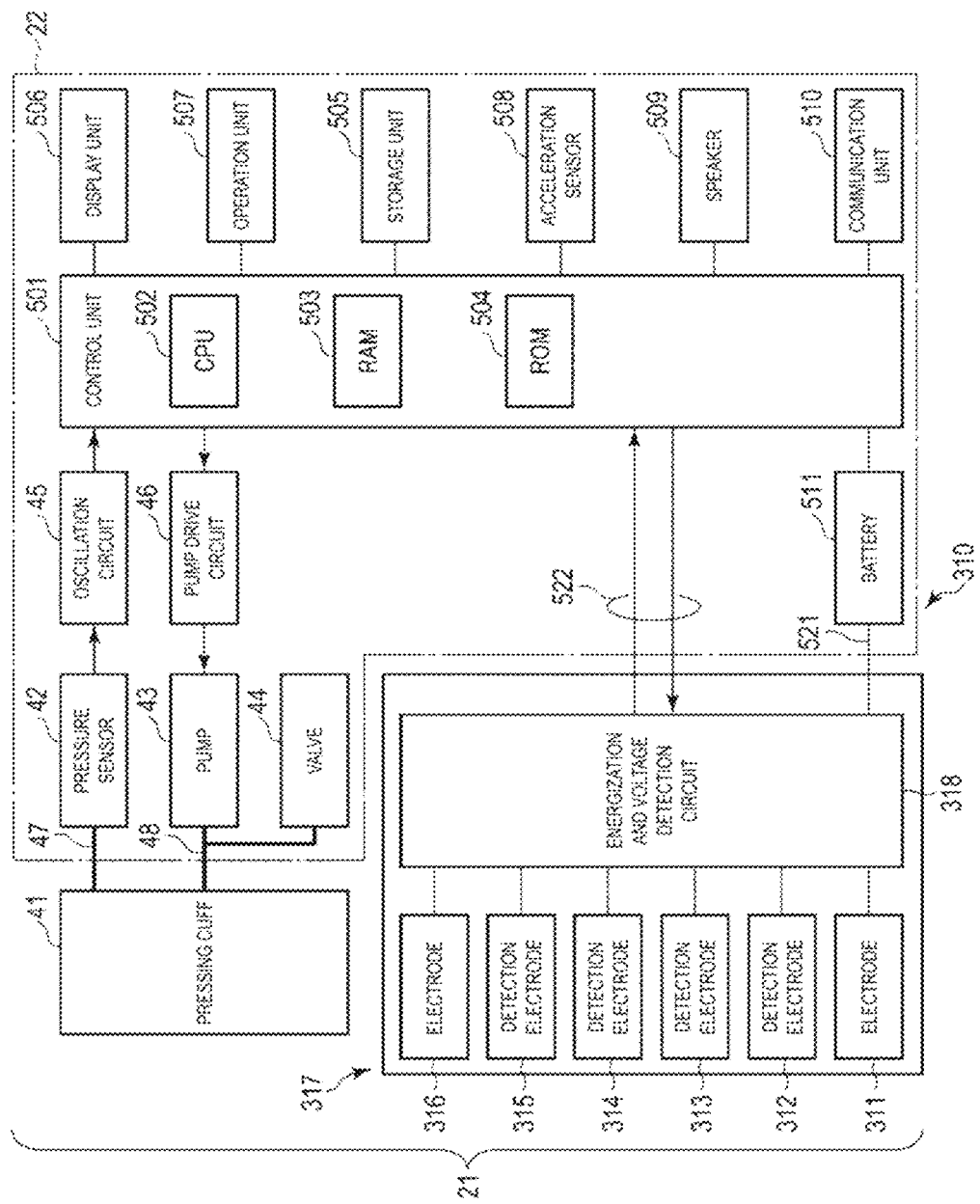
[Fig. 5]

[Fig. 6]
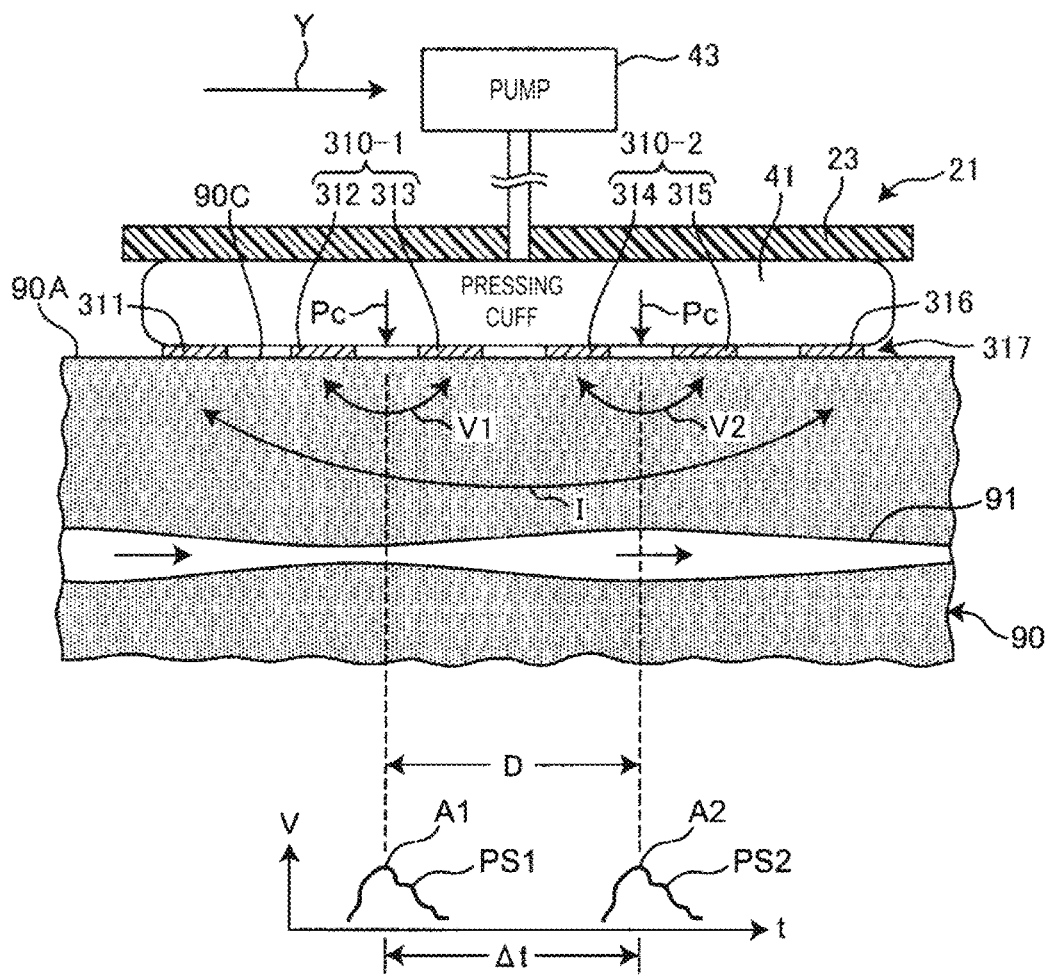

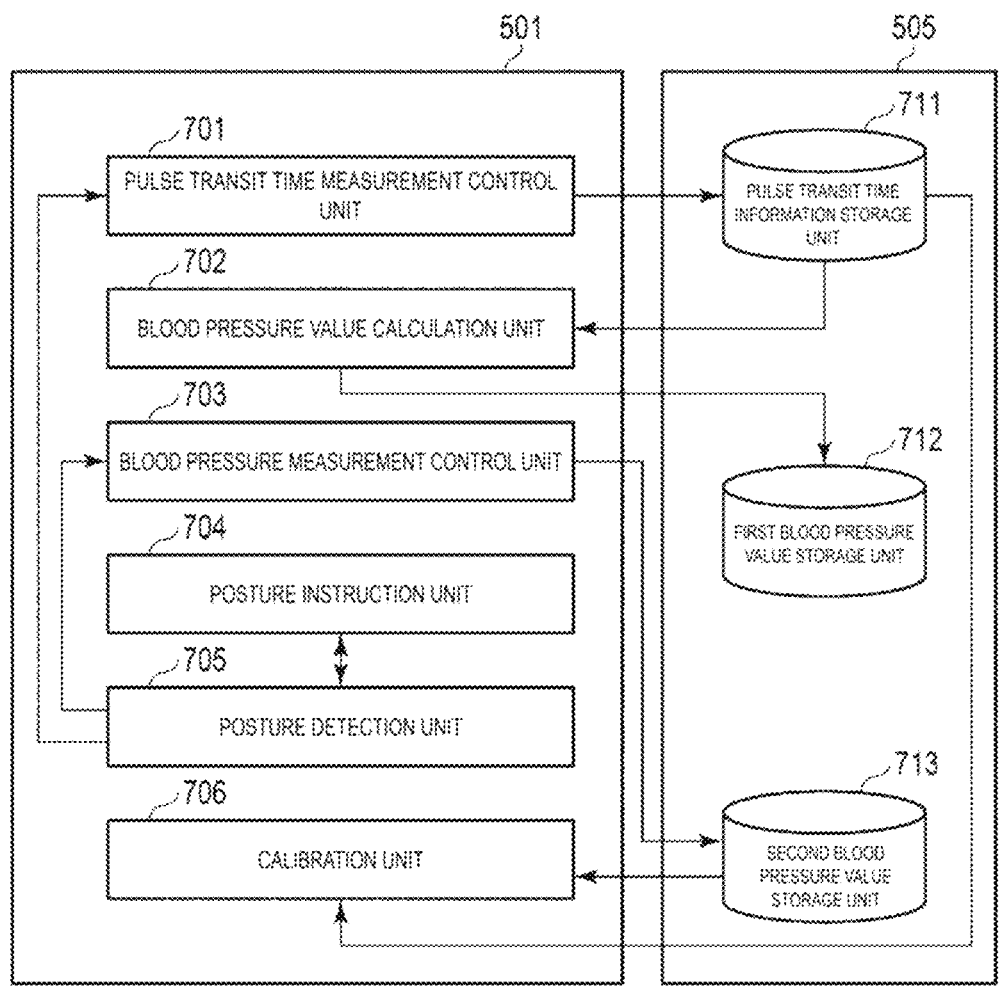
[Fig. 7]

[Fig. 8]
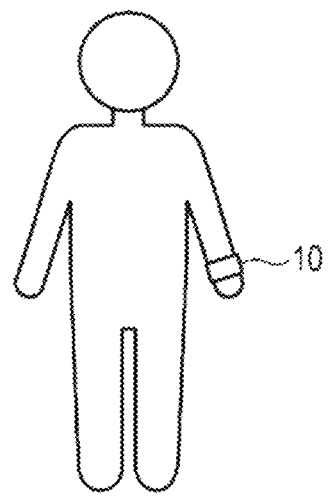
[Fig. 9]
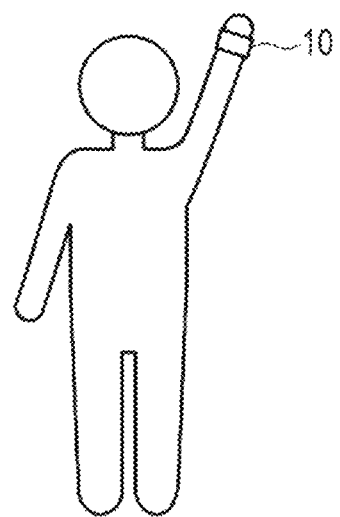

[Fig. 10]
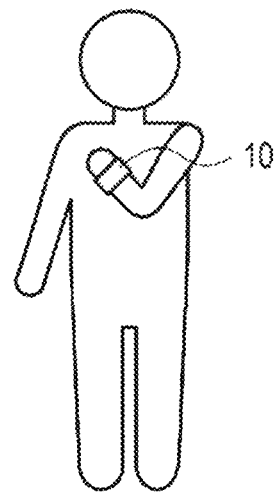

[Fig. 11]
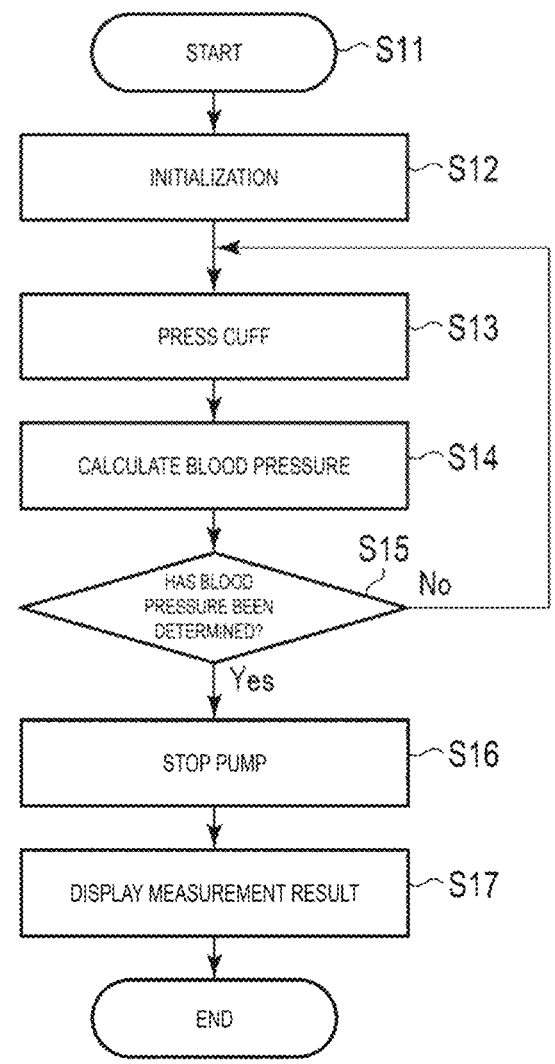

[Fig. 12]
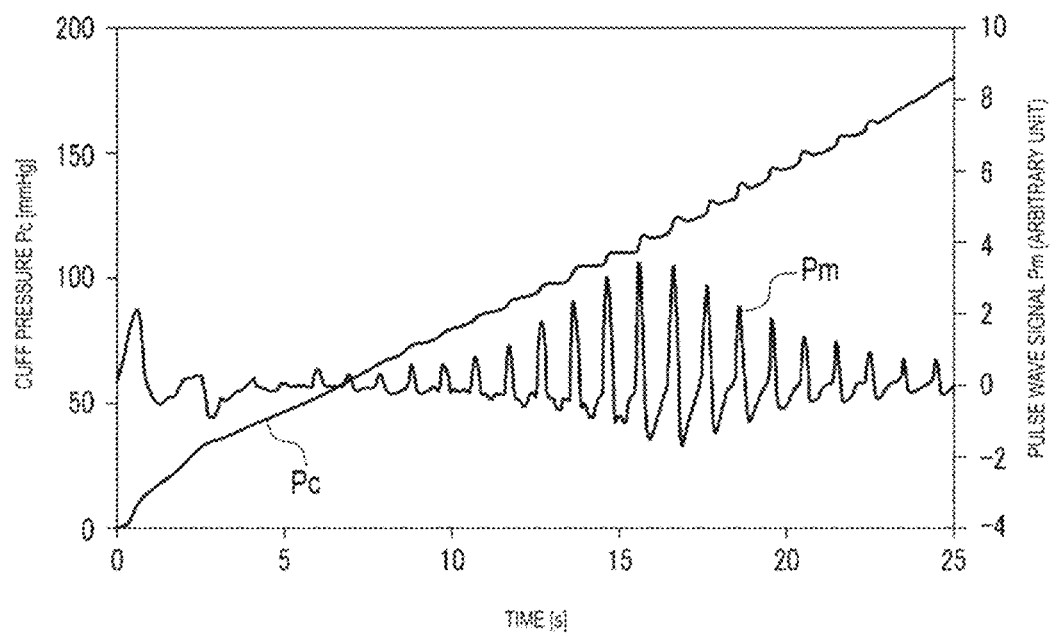

[Fig. 13]
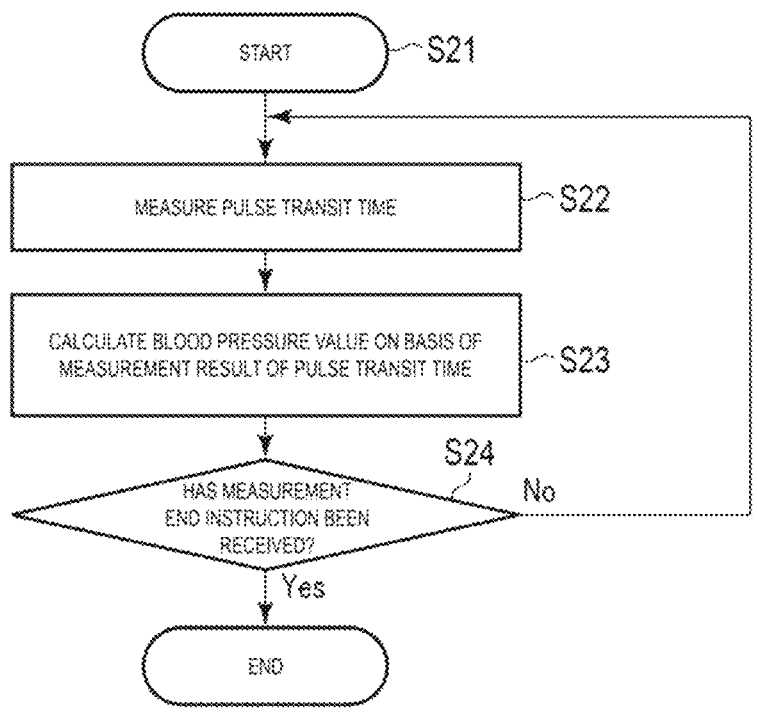

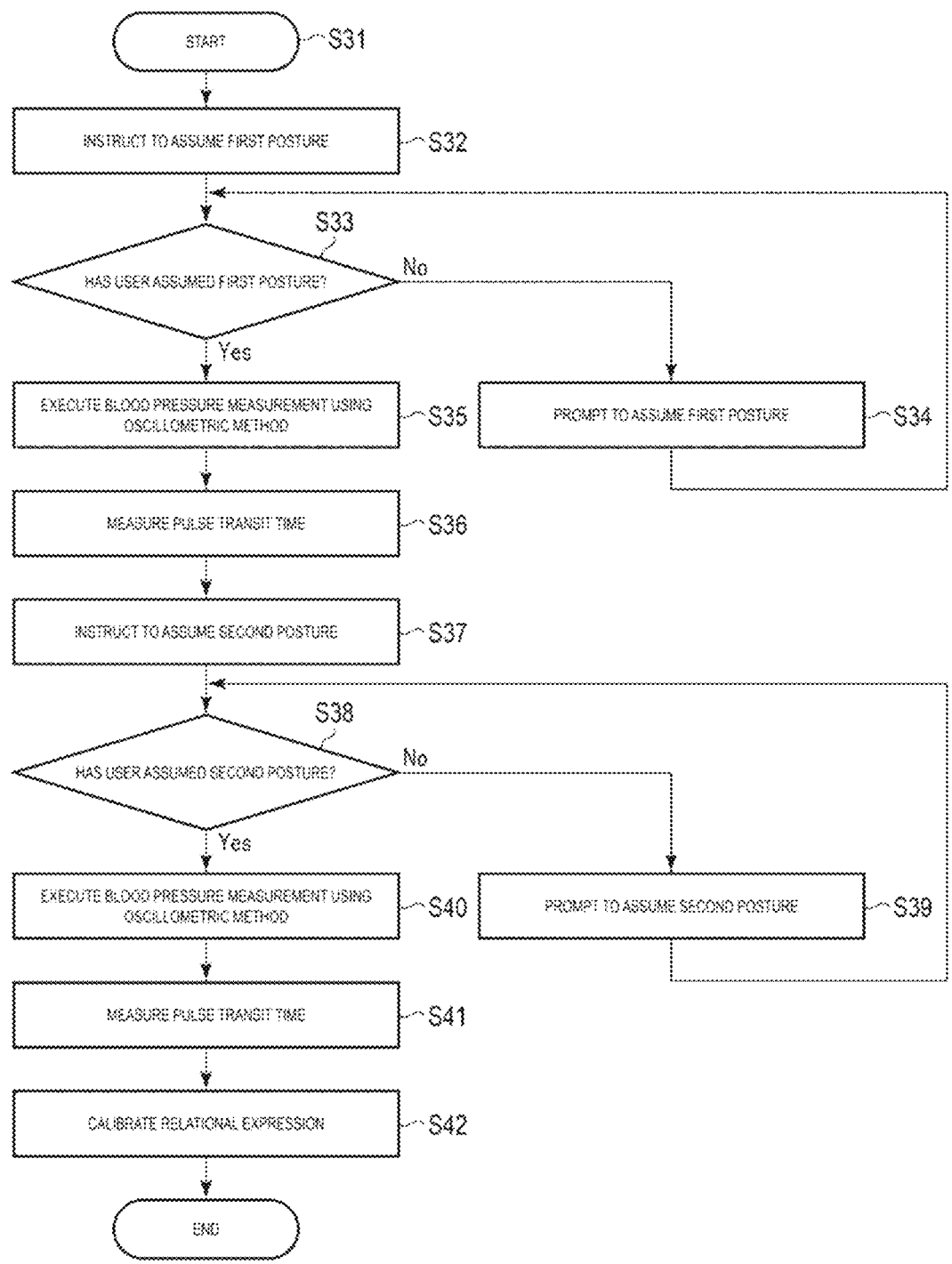
[Fig. 14]

BLOOD PRESSURE MEASUREMENT DEVICE

TECHNICAL FIELD

The present invention relates to a blood pressure measurement device that non-invasively measures blood pressure.

BACKGROUND ART

It is known that there is a correlation between blood pressure and a pulse transit time (PTT), which is a time required for a pulse wave to propagate between two points in an artery.

Patent Literature 1 discloses a blood pressure measurement device that measures blood pressure using the above correlation. This blood pressure measurement device calculates the pulse transit time on the basis of an output of an electrocardiographic (ECG) sensor attached to a user's torso and an output of a photoplethysmographic (PPG) sensor attached to the user's ear and calculates a blood pressure value using the calculated pulse transit time and a relational expression representing the above correlation.

CITATION LIST

Patent Literature

Patent Literature 1: JP 5984088 B

SUMMARY OF INVENTION

Technical Problem

Since the correlation between PTT and blood pressure varies for each individual, it is necessary to calibrate the relational expression for each user. In the blood pressure measurement device disclosed in Patent Literature 1, in order to calibrate the relational expression, PTT and blood pressure are simultaneously measured while changing the blood pressure by applying an exercise load or a mental load to the user. For this reason, a burden on the user regarding the calibration of the relational expression increases, and it takes time to perform the calibration of the relational expression.

The present invention has been made in view of the above circumstances, and an object thereof is to provide a blood pressure measurement device in which a burden on a user can be reduced and calibration of a relational expression can be performed in a short time.

Solution to Problem

The present invention adopts the following configurations in order to solve the above problems.

A blood pressure measurement device according to one aspect includes: a blood pressure measurement unit configured to measure blood pressure at a measurement target site of a measurement target subject; a pulse transit time measurement unit configured to measure a pulse transit time at the measurement target site of the measurement target subject; a blood pressure value calculation unit configured to calculate a blood pressure value, on the basis of measurement results of the pulse transit time and a relational expression representing a correlation between the pulse transit time and the blood pressure; a posture instruction unit configured to instruct the measurement target subject to assume a plurality of postures in which height positions of the measurement target site with respect to a heart of the measurement target subject are different from each other; and a calibration unit configured to calibrate the relational expression, on the basis of the blood pressure measured by the blood pressure measurement unit and the pulse transit time measured by the pulse transit time measurement unit, for each of the plurality of postures.

According to the above configuration, the user only needs to assume several postures when the calibration of the relational expression used for the blood pressure measurement based on the pulse transit time is performed. Therefore, a burden on the user regarding the calibration of the relational expression can be reduced, and the relational expression can be calibrated in a short time.

In one aspect, the posture instruction unit may specify, as the plurality of postures, a posture in which the measurement target site is lower than the heart of the measurement target subject and a posture in which the measurement target site is higher than the heart.

According to the above configuration, two different measurement result sets (each measurement result set has pulse transit time measurement results and blood pressure measurement results) are acquired. As a result, the calibration of the relational expression can be performed well. For example, when the number of parameters related to the relational expression is two, the relational expression can be reliably calibrated.

In one aspect, the posture instruction unit may specify, as the plurality of postures, a posture in which the measurement target site is at the same height as the heart of the measurement target subject. The posture in which the measurement target site is at the same height as the heart is a posture suitable for the blood pressure measurement. Measurement results obtained by performing the measurement in this posture are highly reliable. For this reason, according to the above configuration, a highly reliable measurement result set is used for the calibration of the relational expression. As a result, reliability of the blood pressure measurement results obtained by the blood pressure measurement based on the pulse transit time is improved.

In one aspect, the blood pressure measurement device may further include a posture detection unit configured to detect whether or not the measurement target subject has assumed a posture specified by the posture instruction unit, and the pulse transit time measurement unit and the blood pressure measurement unit each may measure the pulse transit time and the blood pressure in a state in which the posture detection unit detects that the measurement target subject has assumed the posture specified by the posture instruction unit.

According to the above configuration, each measurement result set is guaranteed to have pulse transit time measurement results and blood pressure measurement results acquired in the same posture. For this reason, the relational expression can be accurately calibrated.

In one aspect, the measurement target site is a wrist. According to this configuration, the measurement target subject can easily assume the plurality of postures in which the height positions of the measurement target site with respect to the heart are different from each other.

Advantageous Effects of Invention

According to the present invention, it is possible to provide a blood pressure measurement device in which a burden on a user can be reduced and calibration of a relational expression can be performed in a short time.

BRIEF DESCRIPTION OF DRAWINGS

FIG. 1 is a schematic diagram illustrating a blood pressure measurement device according to one embodiment.

FIG. 2 is a perspective view illustrating an external appearance of the blood pressure measurement device shown in FIG. 1.

FIG. 3 is a cross-sectional view illustrating the blood pressure measurement device shown in FIG. 1.

FIG. 4 is a diagram illustrating a positional relationship between an electrode group shown in FIG. 2 and a radial artery in a worn state.

FIG. 5 is a block diagram illustrating a hardware configuration of a control system of the blood pressure measurement device shown in FIG. 1.

FIG. 6 is a diagram explaining a method of measuring a pulse transit time in the blood pressure measurement device shown in FIG. 1.

FIG. 7 is a block diagram illustrating a software configuration of the blood pressure measurement device shown in FIG. 1.

FIG. 8 is a diagram showing an example of a posture specified by a posture instruction unit shown in FIG. 7.

FIG. 9 is a diagram showing another example of a posture specified by the posture instruction unit shown in FIG. 7.

FIG. 10 is a diagram showing a further example of a posture specified by the posture instruction unit shown in FIG. 7.

FIG. 11 is a flowchart illustrating a procedure of blood pressure measurement using an oscillometric method according to one embodiment.

FIG. 12 is a diagram illustrating changes in cuff pressure and a pulse wave signal in blood pressure measurement using the oscillometric method.

FIG. 13 is a flowchart illustrating a procedure of blood pressure measurement based on a pulse transit time according to one embodiment.

FIG. 14 is a flowchart illustrating a procedure of calibration of a relational expression according to one embodiment.

DESCRIPTION OF EMBODIMENTS

Hereinafter, an embodiment of the present invention will be described with reference to the drawings.

Application Example

With reference to FIG. 1, an example of a case to which the present invention is applied will be described. FIG. 1 schematically shows a blood pressure measurement device 10 according to one embodiment. The blood pressure measurement device 10 is a wearable device and is worn on a wrist serving as a measurement target site of a user. The blood pressure measurement device 10 includes a belt unit 20, a first blood pressure measurement unit 30, a second blood pressure measurement unit 40, a posture instruction unit 50, and a calibration unit 60.

The belt unit 20 is a member that is wound around the user's wrist. The first blood pressure measurement unit 30, the second blood pressure measurement unit 40, the posture instruction unit 50, and the calibration unit 60 are mounted on the belt unit 20.

The first blood pressure measurement unit 30 performs blood pressure measurement based on a pulse transit time.

Specifically, the first blood pressure measurement unit 30 measures the pulse transit time at the user's wrist and calculates a blood pressure value on the basis of measurement results of the pulse transit time. The first blood pressure measurement unit 30 can perform continuous blood pressure measurement for obtaining the blood pressure value for each beat. The second blood pressure measurement unit 40 performs blood pressure measurement using a method different from that of the first blood pressure measurement unit 30. The second blood pressure measurement unit 40 is based on, for example, an oscillometric method or a Korotkoff method and performs the blood pressure measurement at a specific timing, for example, in response to an operation performed by the user. The second blood pressure measurement unit 40 cannot perform continuous blood pressure measurement, but can measure the blood pressure more accurately than the first blood pressure measurement unit 30.

The first blood pressure measurement unit 30 includes a pulse transit time measurement unit 31 and a blood pressure value calculation unit 32. The pulse transit time measurement unit 31 includes two pulse wave sensors provided on the belt unit 20 and non-invasively measures the pulse transit time using these pulse wave sensors. In the present embodiment, the pulse transit time corresponds to a time required for a pulse wave to propagate a distance between the pulse wave sensors on the wrist.

The blood pressure value calculation unit 32 calculates the blood pressure value on the basis of the pulse transit time measured by the pulse transit time measurement unit 31 and a relational expression representing a correlation between the pulse transit time and the blood pressure. An example of the relational expression is shown below.

$$SBP = A_1/PTT^2 + A_2 \quad (1)$$

Here, SBP represents systolic blood pressure, PTT represents the pulse transit time, and $A_1$ and $A_2$ are parameters. The parameters $A_1$ and $A_2$ are determined by the calibration unit 60.

The pulse transit time measurement unit 31 can obtain the pulse transit time for each beat, and therefore the blood pressure value calculation unit 32 can obtain the blood pressure value for each beat.

The posture instruction unit 50 instructs the user to assume a plurality of postures in which height positions of the wrist with respect to the heart are different from each other. When the number of the parameters included in the relational expression is N, at least two measurement result sets (sets including pulse transit time measurement results and blood pressure measurement results) are required. For example, when the relational expression (1) is used, at least two measurement result sets are required. However, in a case in which two blood pressure measurement values included respectively in the two measurement result sets are the same, the parameters $A_1$ and $A_2$ cannot be uniquely determined.

It is generally known that a blood pressure measurement value deviates from an original value (a measurement value obtained in a case in which the heart and the measurement target site are at the same height level) in accordance with a difference in height between the heart and the measurement target site (the wrist in this example). This is a result of gravity. For example, when the difference in height between the heart and the measurement target site is 10 cm, a difference in blood pressure of about 8 mmHg occurs. Similarly, a measurement value of the pulse transit time deviates from an original value in accordance with the difference in height between the heart and the measurement target site.

In the present embodiment, since the blood pressure is measured in each of the plurality of postures in which the height positions of the wrist with respect to the heart are different from each other, different blood pressure measurement values are acquired. As an example, the posture instruction unit 50 first instructs the user to assume a posture in which the user's hand wearing the blood pressure measurement device 10 is lowered. Then, measurement performed by the pulse transit time measurement unit 31 and measurement performed by the second blood pressure measurement unit 40 are executed with the user's hand lowered, and thus a set of the measurement result of the pulse transit time and the measurement result of the blood pressure is acquired. Next, the posture instruction unit 50 instructs the user to assume a posture in which the hand wearing the blood pressure measurement device 10 is raised. Then, measurement performed by the pulse transit time measurement unit 31 and measurement performed by the second blood pressure measurement unit 40 are executed with the user's hand raised, and thus a set of the measurement result of the pulse transit time and the measurement result of the blood pressure is acquired. In the state in which the user's hand is lowered, the wrist is positioned lower than the heart, and a blood pressure measurement value higher than the original value can be obtained. On the other hand, in the state in which the user's hand is raised, the wrist is positioned higher than the heart, and a blood pressure measurement value lower than the original value can be obtained. For this reason, when the blood pressure measurement is performed in the state in which the user's hand is lowered and in the state in which the user's hand is raised, two different blood pressure measurement values can be reliably acquired.

The calibration unit 60 performs calibration of the above relational expression (1) on the basis of a plurality of measurement result sets acquired from each of the plurality of postures. For example, the calibration unit 60 determines the parameters $A_1$ and $A_2$ on the basis of the plurality of measurement result sets by applying a fitting method such as a least squares method.

After the calibration of the relational expression (1) performed by the calibration unit 60 is completed, the first blood pressure measurement unit 30 can perform continuous blood pressure measurement.

As described above, the blood pressure measurement device 10 instructs the user to sequentially assume the plurality of postures in which the height positions of the wrist with respect to the heart are different from each other, measures the pulse transit time and the blood pressure in each of the plurality of postures, and calibrates the relational expression on the basis of the measurement results of the pulse transit time and the blood pressure. Thus, when the relational expression is calibrated, the user may change the posture at that location. Therefore, a burden on the user regarding the calibration of the relational expression decreases, and the relational expression can be calibrated in a short time.

Further, the postures described above include the posture in which the hand wearing the blood pressure measurement device 10 is lowered and the posture in which the hand is raised. Thus, two different blood pressure measurement values can be reliably acquired, and the relational expression can be calibrated successfully.

Hereinafter, the blood pressure measurement device 10 will be described more specifically.

Configuration Example

Hardware Configuration

An example of a hardware configuration of the blood pressure measurement device 10 according to the present embodiment will be described with reference to FIGS. 2 to 6.

FIG. 2 shows an external appearance of the blood pressure measurement device 10 when viewed obliquely, and FIG. 3 schematically shows a cross-section perpendicular to a longitudinal direction of a left wrist 90 in a state in which the blood pressure measurement device 10 is worn on the left wrist 90.

As shown in FIG. 2, the blood pressure measurement device 10 includes a belt 21, a main body 22, and an impedance measurement unit 310. The belt 21 and the main body 22 form the belt unit 20 shown in FIG. 1.

The belt 21 is a belt-shaped member that is worn around the left wrist 90 and may be called by another name such as "band" or "cuff." The belt 21 has an inner circumferential surface 21A and an outer circumferential surface 21B. The inner circumferential surface 21A is a surface that comes into contact with the left wrist 90 of the user in a state in which the user wears the blood pressure measurement device 10 (hereinafter, simply referred to as a "worn state"), and the outer circumferential surface 21B is a surface on a side opposite to the inner circumferential surface 21A. A width of the belt 21 is set to be about 30 mm in this example. The width is a dimension of the belt 21 in a width direction thereof. The width direction of the belt 21 corresponds to the longitudinal direction of the left wrist 90 indicated by an arrow Y.

The main body 22 is provided by integrally molding it with an end portion 21E in a circumferential direction of the belt 21. Further, the belt 21 and the main body 22 may be separately formed, and the main body 22 may be attached to the belt 21 using an engaging member (for example, a hinge or the like). In this example, as shown in FIG. 3, a portion of the belt 21 on which the main body 22 is disposed is expected to be positioned on a surface 90B on a back side of the left wrist 90 in the worn state. FIG. 3 shows a radial artery 91 passing near a surface 90A on a palm side of the left wrist 90.

The main body 22 is formed to be thin and compact not to disturb daily activities of the user. In this example, the main body 22 has a contour having a quadrangular truncated pyramid shape, protruding outward from the belt 21.

As shown in FIG. 2, a display unit 506 is provided on a top surface 22A of the main body 22. Also, an operation unit 507 is provided along a side surface 22F of the main body 22.

A bottom surface 22B (a surface on an inner circumferential side) of the main body 22 is connected to the other end portion 21F in the circumferential direction of the belt 21 using a three-fold buckle 24. The buckle 24 includes: a first plate-shaped member 25 disposed on an outer circumferential side thereof and a second plate-shaped member 26 disposed on the inner circumferential side thereof. One end portion 25E of the first plate-shaped member 25 is rotatably attached to the main body 22 via a connecting rod 27 extending in the width direction of the belt 21. The other end portion 25F of the first plate-shaped member 25 is rotatably attached to one end portion 26F of the second plate-shaped member 26 via a connecting rod 28 extending in the width direction of the belt 21. The other end portion 26E of the second plate-shaped member 26 is fixed to the end portion 21F of the belt 21 using a fixing portion 29. Further, an attached position of the fixing portion 29 in the circumferential direction of the belt 21 is variably set in advance in accordance with a circumferential length of the left wrist 90 of the user. As a result, the belt 21 is generally formed in substantially an annular shape, and the bottom surface 22B of the main body 22 and the end portion 21F of the belt 21 are formed to be openable and closable in a direction indicated by an arrow B due to the buckle 24.

The impedance measurement unit 310 is provided at a portion between the end portion 21E and the end portion 21F of the belt 21. The impedance measurement unit 310 includes an electrode group 317 and an energization and voltage detection circuit 318 (shown in FIG. 5). The electrode group 317 is disposed on the inner circumferential surface 21A of the belt 21. The electrode group 317 includes six plate-shaped or sheet-shaped electrodes 311 to 316 separated from each other in the width direction of the belt 21. As shown in FIG. 3, the portion of the belt 21 on which the electrode group 317 is disposed faces the radial artery 91 of the left wrist 90 in the worn state.

When the blood pressure measurement device 10 is worn on the left wrist 90, the user passes his or her left hand through the belt 21 in a direction indicated by an arrow A in FIG. 2, with the buckle 24 opened to increase a diameter of a ring of the belt 21. Then, as shown in FIG. 3, the user adjusts an angular position of the belt 21 with respect to the left wrist 90, and positions the impedance measurement unit 310 of the belt 21 over the radial artery 91 passing through the left wrist 90. Thus, the electrode group 317 of the impedance measurement unit 310 comes into contact with a portion 90C of the left wrist 90 corresponding to the radial artery 91. In this state, the user closes and fixes the buckle 24. In this way, the user wears the blood pressure measurement device 10 on the left wrist 90.

As shown in FIG. 3, the belt 21 includes a strip 23 forming the outer circumferential surface 21B, and a pressing cuff 41 as a pressing member attached along the inner circumferential surface of the strip 23. In this example, the strip 23 is made of a plastic material, is flexible in a thickness direction thereof, and is substantially non-stretchable in the circumferential direction thereof. In this example, the pressing cuff 41 is configured as a fluid bag by causing two stretchable polyurethane sheets to face each other in the thickness direction and welding their circumferential edges. As described above, the electrode group 317 of the impedance measurement unit 310 is disposed at the portion of the inner circumferential surface 21A (inner circumferential surface of the pressing cuff 41) of the belt 21 (corresponding to the radial artery 91 of the left wrist 90).

As shown in FIG. 4, in the worn state, the electrode group 317 of the impedance measurement unit 310 is arranged in the longitudinal direction (corresponding to the width direction of the belt 21) of the left wrist 90 to correspond to the radial artery 91 of the left wrist 90. The electrode group 317 includes: a pair of energization electrodes 311 and 316 which are disposed on both sides of the belt 21 in the width direction; and a pair of first detection electrodes 312 and 313 and a pair of second detection electrodes 314 and 315 for voltage detection which are disposed between the pair of electrodes 311 and 316. The pair of first detection electrodes 312 and 313 form a first pulse wave sensor 310-1. The pair of second detection electrodes 314 and 315 form a second pulse wave sensor 310-2. The pair of second detection electrodes 314 and 315 are disposed on a downstream side of a blood flow in the radial artery 91 from the pair of first detection electrodes 312 and 313. In the width direction of the belt 21, a distance D (see FIG. 6) between the center of the pair of first detection electrodes 312 and 313 and a center of the pair of second detection electrodes 314 and 315 is set to 20 mm in this example. This distance D corresponds to a substantial interval between the first pulse wave sensor 310-1 and the second pulse wave sensor 310-2. Further, in the width direction of the belt 21, a distance between the pair of first detection electrodes 312 and 313 and a distance between the pair of second detection electrodes 314 and 315 are set to 2 mm in this example.

Such an electrode group 317 may be configured to be flat. Therefore, in the blood pressure measurement device 10, the belt 21 can be configured to be thin as a whole.

FIG. 5 shows a hardware configuration of a control system of the blood pressure measurement device 10. In addition to the operation unit 507 and the display unit 506 described above, a control unit 501, a storage unit 505, an acceleration sensor 508, a speaker 509, a communication unit 510, a battery 511, a pressure sensor 42, a pump 43, a valve 44, an oscillation circuit 45, and a pump drive circuit 46 are mounted on the main body 22 of the blood pressure measurement device 10.

The control unit 501 includes a central processing unit (CPU) 502, a random access memory (RAM) 503, a read only memory (ROM) 504, and the like and controls each constituent element. The storage unit 505 is, for example, an auxiliary storage device such as a semiconductor memory (for example, a flash memory) and non-temporarily stores programs executed by the control unit 501 (for example, including a pulse transit time measurement program, a blood pressure value calculation program, a blood pressure measurement program, and a relational expression calibration program), setting data necessary for executing the programs, blood pressure measurement result data, and the like. A storage medium included in the storage unit 505 is, to enable computers, other devices, machines, or the like to read information such as recorded programs, a medium that stores information such as the programs, by using electrical, magnetic, optical, mechanical, or chemical actions. Also, the pulse transit time measurement program, the blood pressure value calculation program, the blood pressure measurement program, and/or the relational expression calibration program may be stored in the ROM 504.

The display unit 506 is an organic light emitting diode (OLED) display in this example and displays: information related to blood pressure measurement such as blood pressure measurement results; and other information, in accordance with a control signal from the control unit 501. Also, the display unit 506 may be, for example, a liquid crystal display (LCD) device. The operation unit 507 includes a push-type button in this example and inputs an operation signal, in accordance with the user's instruction to start or stop the blood pressure measurement, to the control unit 501.

The acceleration sensor 508 is, for example, a triaxial acceleration sensor and outputs an acceleration signal representing acceleration in three directions orthogonal to each other. The speaker 509 emits sound on the basis of an acoustic signal from the control unit 501.

The communication unit 510 is a communication interface for communicating with an external device. The communication unit 510 receives information from the control unit 501 and transmits the information to the external device via a network. Further, the communication unit 510 receives information from the external device via the network and transfers the information to the control unit 501. Communication via the network may be wireless or wired. The network is the Internet, but is not limited thereto. The network may be another type of network such as a local area network (LAN) in a hospital. Also, the communication unit 510 may directly wirelessly communicate with an external device (for example, a smartphone owned by the user). As a wireless system, for example, Bluetooth (trade name), Bluetooth Low Energy (BLE), or the like can be adopted. The communication unit 510 may include a terminal such as a micro Universal Serial Bus (USB) connector and may be connected to an external device by a cable such as a USB cable to communicate with the external device.

The pump 43 and the valve 44 are connected to the pressing cuff 41 via a pipe 48, and the pressure sensor 42 is connected to the pressing cuff 41 via a pipe 47. Also, the pipes 47 and 48 may be a single common pipe. The pump 43 is a piezoelectric pump in this example and supplies air as a fluid to the pressing cuff 41 through a pipe 47, in order to increase a pressure inside the pressing cuff 41. The valve 44 is mounted on the pump 43, and opening and closing of the valve 44 is configured to be controlled as the pump 43 is turned on and off. Specifically, the valve 44 closes when the pump 43 is turned on and opens when the pump 43 is turned off. With the valve 44 opened, the pressing cuff 41 is in communication with the atmosphere. The valve 44 has a function of a check valve, and air does not flow back through it. The pump drive circuit 46 drives the pump 43 on the basis of a control signal provided from the control unit 501.

The pressure sensor 42 is a piezoresistive pressure sensor in this example, detects the pressure in the pressing cuff 41 (hereinafter, also referred to as a cuff pressure), and outputs an electric signal representing the cuff pressure. The cuff pressure is, for example, a pressure based on the atmospheric pressure as a reference. The oscillation circuit 45 oscillates on the basis of the electric signal from the pressure sensor 42 and outputs, to the control unit 501, a frequency signal having a frequency in accordance with the electric signal. In this example, the output of the pressure sensor 42 is used to control the pressure of the pressing cuff 41 and to calculate a blood pressure value (including a systolic blood pressure (SBP) and a diastolic blood pressure (DBP)) using an oscillometric method.

The battery 511 supplies electric power to the constituent elements mounted on the main body 22. In this example, the battery 511 supplies power to the control unit 501, the storage unit 505, the acceleration sensor 508, the communication unit 510, the display unit 506, the pressure sensor 42, the pump 43, the valve 44, the oscillation circuit 45, and the pump drive circuit 46. Further, the battery 511 supplies electric power to the energization and voltage detection circuit 318 of the impedance measurement unit 310 through a wiring 521. The wiring 521, along with a signal wiring 522, is provided to extend between the main body 22 and the impedance measurement unit 310 in the circumferential direction of the belt 21 while it is sandwiched between the strip 23 of the belt 21 and the pressing cuff 41.

The energization and voltage detection circuit 318 is controlled by the control unit 501. As shown in an upper part of FIG. 6, the energization and voltage detection circuit 318 causes a high frequency constant current I to flow between the pair of electrodes 311 and 316 during its operation. In this example, a frequency of the current I is 50 kHz and a current value thereof is 1 mA. In this state, the energization and voltage detection circuit 318 detects: a voltage signal V1 between the pair of first detection electrodes 312 and 313 forming the first pulse wave sensor 310-1; and a voltage signal V2 between the pair of second detection electrodes 314 and 315 forming the second pulse wave sensor 310-2. These voltage signals V1 and V2 represent changes in electrical impedance due to the pulse wave of the blood flow in the radial artery 91 at a portion of a surface 90A on a palm side of the left wrist 90 where the first pulse wave sensor 310-1 and the second pulse wave sensor 310-2 face. The energization and voltage detection circuit 318 rectifies, amplifies, and filters these voltage signals V1 and V2 and, as shown in a lower part of FIG. 6, outputs, in time series, the first pulse wave signal PS1 and the second pulse wave signal PS2 having a ridge waveform. In this example, the voltage signals V1 and V2 are about 1 mV. Also, peaks A1 and A2 of the first pulse wave signal PS1 and the second pulse wave signal PS2 are about 1 volt in this example.

If a pulse wave velocity (PWV) of the blood flow in the radial artery 91 is in the range of 1000 cm/s to 2000 cm/s, a substantial distance D between the first pulse wave sensor 310-1 and the second pulse wave sensor 310-2 is 20 mm, and thus a time difference Δt between the first pulse wave signal PS1 and the second pulse wave signal PS2 is in the range of 1.0 ms to 2.0 ms.

The first blood pressure measurement unit 30 shown in FIG. 1 includes, as hardware, the impedance measurement unit 310 (the electrode group 317 and the energization and voltage detection circuit 318). The second blood pressure measurement unit 40 shown in FIG. 1 includes, as hardware, the pressing cuff 41, the pressure sensor 42, the pump 43, the valve 44, the oscillation circuit 45, and the pump drive circuit 46 shown in FIG. 5.

Also, with respect to a specific hardware configuration of the blood pressure measurement device 10, constituent elements can be omitted, replaced, or added as appropriate in accordance with embodiments. For example, the control unit 501 may include a plurality of processors. Instead of the acceleration sensor 508 or in addition to the acceleration sensor 508, the blood pressure measurement device 10 may include a gyro sensor.

Software Configuration

An example of a software configuration of the blood pressure measurement device 10 according to the present embodiment will be described with reference to FIG. 7.

FIG. 7 shows a software configuration of the blood pressure measurement device 10. The blood pressure measurement device 10 includes: a pulse transit time measurement control unit 701, a blood pressure value calculation unit 702, a blood pressure measurement control unit 703, a posture instruction unit 704, a posture detection unit 705, a calibration unit 706, a pulse transit time information storage unit 711, a first blood pressure value storage unit 712, and a second blood pressure value storage unit 713. The pulse transit time measurement control unit 701, the blood pressure value calculation unit 702, the blood pressure measurement control unit 703, the posture instruction unit 704, the posture detection unit 705, and the calibration unit 706 execute the following processing, as the control unit 501 of the blood pressure measurement device 10 executes a program stored in the storage unit 505. When the control unit 501 executes the program, the control unit 501 loads the program in the RAM 503. Then, the control unit 501 causes the CPU 502 to interpret and execute the program loaded in the RAM 503 to control the constituent elements. The pulse transit time information storage unit 711, the first blood pressure value storage unit 712, and the second blood pressure value storage unit 713 are realized by the storage unit 505.

The pulse transit time measurement control unit 701 controls the energization and voltage detection circuit 318 in order to measure the pulse transit time. Specifically, the pulse transit time measurement control unit 701 sends an instruction signal for flowing a current between the pair of electrodes 311 and 316 to the energization and voltage detection circuit 318 and acquires, from the energization and voltage detection circuit 318, the voltage signal V1 between the pair of first detection electrodes 312 and 313 and the voltage signal V2 between the pair of second detection electrodes 314 and 315, which are detected in a state in which the current flows between the pair of electrodes 311 and 316. Then, the pulse transit time measurement control unit 701 generates the first pulse wave signal PS1 on the basis of the voltage signal V1, generates the second pulse wave signal PS2 on the basis of the voltage signal V2, and calculates the pulse transit time on the basis of the first pulse wave signal PS1 and the second pulse wave signal PS2. For example, the pulse transit time measurement control unit 701 calculates the time difference Δt between the peak A1 of the first pulse wave signal PS1 and the peak A2 of the second pulse wave signal PS2 as the pulse transit time. The pulse transit time measurement control unit 701 stores the pulse transit time information representing the calculated pulse transit time, in association with time information, in the pulse transit time information storage unit 711.

The blood pressure value calculation unit 702 corresponds to the blood pressure value calculation unit 32 shown in FIG. 1. The blood pressure value calculation unit 702 reads the pulse transit time calculated by the pulse transit time measurement control unit 701 from the pulse transit time information storage unit 711 and calculates the blood pressure value on the basis of the read pulse transit time and a relational expression (for example, the above relational expression (1)). The blood pressure value calculation unit 702 stores the blood pressure value information representing the calculated blood pressure value, in association with time information, in the first blood pressure value storage unit 712.

The blood pressure measurement control unit 703 controls the pump drive circuit 46 to execute the blood pressure measurement using the oscillometric method. Specifically, the blood pressure measurement control unit 703 drives the pump 43 via the pump drive circuit 46. Thus, supply of air to the pressing cuff 41 is started. The pressing cuff 41 is inflated, which compresses the user's left wrist 90. The blood pressure measurement control unit 703 monitors the cuff pressure using the pressure sensor 42. The blood pressure measurement control unit 703 calculates the blood pressure value using the oscillometric method on the basis of a pressure signal output from the pressure sensor 42 in a pressurizing process of supplying air to the pressing cuff 41. Although the blood pressure value includes the systolic blood pressure (SBP) and the diastolic blood pressure (DBP), but is not limited thereto. The blood pressure measurement control unit 703 stores the calculated blood pressure value, in association with time information, in the second blood pressure value storage unit 713. The blood pressure measurement control unit 703 can calculate the pulse rate and the blood pressure value at the same time. The blood pressure measurement control unit 703 stops the pump 43 via the pump drive circuit 46 when calculation of the blood pressure value is completed. Thus, air is exhausted from the pressing cuff 41 through the valve 44.

The posture instruction unit 704 corresponds to the posture instruction unit 50 shown in FIG. 1. The posture instruction unit 704 instructs the user to sequentially assume a plurality of postures to obtain measurement results of the pulse transit time and measurement results of the blood pressure in each of the plurality of postures in which the height positions of the measurement target site with respect to the heart are different from each other. The instruction is given by display, sound, vibration, or the like.

In the present embodiment, the posture instruction unit 704 specifies the postures to be assumed. Examples of the postures to be assumed include a posture in which the left wrist is lower than the heart of the user, a posture in which the left wrist is higher than the heart, and a posture in which the left wrist is at the same height as the heart. The posture in which the left wrist is lower than the heart of the user is, for example, the posture in which the left arm is lowered as shown in FIG. 8. The posture in which the left wrist is higher than the heart is, for example, the posture in which the left arm is raised as shown in FIG. 9. The posture in which the left wrist is at the same height as the heart is, for example, the posture in which the left hand is placed on his or her chest as shown in FIG. 10. FIGS. 8 to 10 show examples in which the user assumes each posture while standing, but the user may assume each posture while sitting. The posture instruction unit 704 may specify either standing or sitting.

The posture detection unit 705 detects the posture of the user on the basis of an output of the sensor (acceleration sensor 508 in this example) provided in the blood pressure measurement device 10. Specifically, the posture detection unit 705 determines whether or not the user has assumed the posture specified by the posture instruction unit 704.

The calibration unit 706 corresponds to the calibration unit 60 shown in FIG. 1. The calibration unit 706 reads the measurement results of the pulse transit time acquired in each of the plurality of postures from the pulse transit time information storage unit 711, reads the measurement results of the blood pressure acquired in each of the plurality of postures from the second blood pressure value storage unit 713, and generates a plurality of measurement result sets. Each measurement result set includes a pulse transit time measurement result and a blood pressure measurement result acquired in one corresponding posture. The calibration unit 706 performs calibration of the relational expression (1) on the basis of the generated measurement result sets. In a case in which the same number of measurement result sets as the number of parameters are acquired, the parameters are determined such that the relational expression satisfies the measurement result sets. In a case in which a larger number of measurement result sets than the number of parameters are acquired, the calibration unit 706 determines the parameters $A_1$ and $A_2$ by applying, for example, the least squares method.

Also, the present embodiment describes an example in which all the functions of the blood pressure measurement device 10 are realized by a general-purpose processor. However, some or all of the functions may be implemented by one or more dedicated processors.

Operation Example

Blood Pressure Measurement Using Oscillometric Method
FIG. 11 shows an operation flow when the blood pressure measurement device 10 performs measurement of blood pressure using the oscillometric method. In each process shown in FIG. 11, the control unit 501 operates as the blood pressure measurement control unit 703.

In step S11 in FIG. 11, the control unit 501 starts blood pressure measurement using the oscillometric method. For example, the control unit 501 receives from the operation unit 507 an operation signal indicating that the user has instructed execution of the blood pressure measurement using the oscillometric method and starts the blood pressure measurement in response to the operation signal.

In step S12, the control unit 501 performs initialization for the blood pressure measurement. For example, the control unit 501 initializes a processing memory area. Further, the control unit 501 stops the pump 43 via the pump drive circuit 46. Along with this, the valve 44 is opened, and the air in the pressing cuff 41 is exhausted. Subsequently, the control unit 501 sets a current output value of the pressure sensor 42 as a reference value for the cuff pressure.

In step S13, the control unit 501 performs control of pressurizing the pressing cuff 41. For example, the control unit 501 drives the pump 43 via the pump drive circuit 46. Along with this, the valve 44 is closed and air is supplied to the pressing cuff 41. As a result, the pressing cuff 41 is inflated, and a cuff pressure Pc gradually increases as shown in FIG. 12. The control unit 501 monitors the cuff pressure Pc with the pressure sensor 42 and acquires a pulse wave signal Pm representing a fluctuation component of an arterial volume.

In step S14 in FIG. 11, the control unit 501 attempts to calculate the blood pressure value (the systolic blood pressure and the diastolic blood pressure) on the basis of the pulse wave signal Pm acquired at this point. If the blood pressure value cannot be calculated yet due to lack of data at this point (No in step S15), the processes of steps S13 to S15 are repeated unless the cuff pressure Pc reaches an upper limit pressure. The upper limit pressure is predetermined from the viewpoint of safety. The upper limit pressure is set to 300 mmHg, for example.

When the blood pressure value can be calculated (Yes in step S15), the control unit 501 stops the pump 43 via the pump drive circuit 46 in step S16. Along with this, the valve 44 is opened, and the air in the pressing cuff 41 is exhausted. In step S17, the control unit 501 displays the blood pressure measurement results on the display unit 506 and records them in the storage unit 505.

Also, the blood pressure value may be calculated not only in the pressurizing process but also in a depressurizing process in which the air in the pressing cuff 41 is exhausted.

(Blood Pressure Measurement Based on Pulse Transit Time)

FIG. 13 shows an operation flow when the blood pressure measurement device 10 performs measurement of blood pressure based on the pulse transit time.

In step S21 in FIG. 13, the control unit 501 starts blood pressure measurement based on the pulse transit time. For example, the control unit 501 receives an operation signal indicating that the user has instructed start of the blood pressure measurement based on the pulse transit time from the operation unit 507 and starts the blood pressure measurement in response to the operation signal.

In step S22, the control unit 501 operates as the pulse transit time measurement control unit 701 to measure the pulse transit time. Specifically, the control unit 501 controls the energization and voltage detection circuit 318 to flow a high frequency constant current between the pair of electrodes 311 and 316 and calculates the pulse transit time on the basis of the first pulse wave signal PS1 acquired by using the first pulse wave sensor 310-1 and the second pulse wave signal PS2 acquired by using the second pulse wave sensor 310-2. For example, the control unit 501 obtains the time difference Δt between the peak A1 of the first pulse wave signal PS1 and the peak A2 of the second pulse wave signal PS2 as the pulse transit time (see FIG. 6).

In step S23, the control unit 501 operates as the blood pressure value calculation unit 702 and calculates a blood pressure value on the basis of the pulse transit time acquired in step S22, using a relational expression representing a correlation between the pulse transit time and blood pressure. The control unit 501 records the measurement results of the blood pressure value in the storage unit 505. For example, the relational expression (1) described above is used.

In step S24, the control unit 501 determines whether or not an operation signal indicating that the user has instructed end of the blood pressure measurement based on the pulse transit time has been received from the operation unit 507. The processes of steps S22 and S23 are repeated until the control unit 501 receives the operation signal. Thus, the blood pressure value for each beat is recorded. When the control unit 501 receives the operation signal, the control unit 501 ends the blood pressure measurement based on the pulse transit time.

In the blood pressure measurement based on the pulse transit time, a physical burden on the user is lighter than in the blood pressure measurement using the oscillometric method, and it is possible to continuously measure the blood pressure for a long period of time.

Further, according to the blood pressure measurement device 10, the blood pressure measurement (estimation) based on the pulse transit time and the blood pressure measurement using the oscillometric method can be performed by an integrated device. Therefore, convenience for the user can be improved.

(Calibration of Relational Expression Used in Blood Pressure Measurement Based on Pulse Transit Time)

FIG. 14 shows an operation flow when the blood pressure measurement device 10 calibrates a relational expression. Here, it is assumed that a relational expression having two parameters such as the relational expression (1) is used for the blood pressure measurement based on the pulse transit time.

In step S31 in FIG. 14, the control unit 501 starts calibration of the relational expression. For example, the calibration of the relational expression is performed when the user starts using the blood pressure measurement device 10. Also, the calibration of the relational expression may be performed every time the user wears the blood pressure measurement device 10 or may be performed periodically.

In step S32, the control unit 501 operates as the posture instruction unit 704 and instructs the user to assume a first posture. For example, the control unit 501 outputs, via the speaker 509, a voice guidance "Please assume a posture in which the arm wearing the device is lowered."

In step S33, the control unit 501 operates as the posture detection unit 705 and determines whether or not the user has assumed the first posture, on the basis of an output of the acceleration sensor 508. In a case in which it cannot be detected that the user has taken the first posture until a predetermined time has elapsed since the instruction in step S32 was output (No in step S33), the control unit 501 operates as the posture instruction unit 704 in step S34 and prompts the user to assume the first posture. For example, the control unit 501 outputs again the voice "Please assume a posture in which the arm wearing the device is lowered" via the speaker 509. Also, the control unit 501 may output a warning sound via the speaker 509.

In a case in which it is detected that the user has assumed the first posture (Yes in step S33), the control unit 501 operates as the blood pressure measurement control unit 703 in step S35 and executes the blood pressure measurement using the oscillometric method. Since the blood pressure measurement using the oscillometric method has been described with reference to FIG. 11, a detailed description thereof will be omitted.

In step S36, the control unit 501 operates as the pulse transit time measurement control unit 701 to measure the pulse transit time. The measurement of the pulse transit time is the same as that described with reference to step S22 in FIG. 13, and thus a detailed description thereof will be omitted. The control unit 501 may measure the pulse transit time for one beat and acquire it as the pulse transit time used for calibration. Also, the control unit 501 may measure pulse transit times of a plurality of beats and acquire an average value thereof as the pulse transit times used for calibration.

In step S37, the control unit 501 operates as the posture instruction unit 704 and instructs the user to assume a second posture. For example, the control unit 501 outputs, via the speaker 509, a voice guidance "Please assume a posture in which the arm wearing the device is raised."

In step S38, the control unit 501 operates as the posture detection unit 705 and determines whether or not the user has assumed the second posture. In a case in which it cannot be detected that the user has assumed the second posture until a predetermined time has elapsed after the instruction of step S37 was output (No in step S38), the control unit 501 operates as the posture instruction unit 704 in step S39 and prompts the user to assume the second posture. In a case in which it is detected that the user has assumed the second posture (Yes in step S38), the control unit 501 operates as the blood pressure measurement control unit 703 in step S40 to execute the blood pressure measurement using the oscillometric method and operates as the pulse transit time measurement control unit 701 in step S41 to measure the pulse transit time. Since the processes of steps S38 to S41 are the same as the processes of steps S33 to S36, respectively, detailed descriptions thereof will be omitted.

In step S42, the control unit 501 operates as the calibration unit 706 to calibrate the relational expression on the basis of: a set of the blood pressure measurement results acquired in step S35 and the pulse transit time measurement results acquired in step S36; and a set of the blood pressure measurement results acquired in step S40 and the pulse transit time measurement results acquired in step S41. In this example, since two sets of measurement results are obtained for two parameters, the parameters are determined such that the relational expression satisfies the two sets of measurement results.

Further, the processing procedure shown in FIG. 11, FIG. 13, or FIG. 14 is merely an example and the processing procedure or the content of each processing can be appropriately changed. For example, in FIG. 14, the pulse transit time may be measured before the blood pressure measurement using the oscillometric method. A process in which a voice guidance "Please maintain that posture" may be added between step S33 and step S35. The measurement may be performed for three or more postures.

Effects

As described above, the blood pressure measurement device 10 according to the present embodiment instructs the user to sequentially assume a plurality of postures in which the height positions of the left wrist with respect to the heart are different from each other, measures the pulse transit time and the blood pressure in each of the plurality of postures, and calibrates the relational expression used for calculating the blood pressure value based on the pulse transit time, on the basis of the measurement results of the pulse transit time and the blood pressure. Thus, when the relational expression is calibrated, the user only needs to change a posture at that location. In this way, no exercise or mental load needs to be applied to the user in order to calibrate the relational expression. Therefore, a burden on the user regarding the calibration of the relational expression decreases, and the relational expression can be calibrated in a short time.

The blood pressure measurement device 10 may specify a posture in which the left wrist is lower than the heart of the user and a posture in which the left wrist is higher than the heart of the user. Thus, two different measurement result sets can be reliably acquired. As a result, the relational expression can be reliably calibrated.

The blood pressure measurement device 10 may specify a posture in which the left wrist is at the same height as the heart. The posture in which the left wrist is at the same height as the heart is a posture suitable for blood pressure measurement. The measurement result obtained by performing the measurement in the posture in which the left wrist is at the same height as the heart is highly reliable. By performing the calibration of the relational expression on the basis of the highly reliable measurement result, the reliability of the blood pressure measurement result obtained by the blood pressure measurement based on the pulse transit time is improved.

The blood pressure measurement device 10 detects whether or not the user has assumed a specified posture. Thus, a measurement result set acquired by measuring the pulse transit time and the blood pressure in the same posture can be generated.

The blood pressure measurement device 10 is worn on a wrist. Thus, the user can easily assume a plurality of postures in which the height positions of the measurement target site with respect to the heart are different from each other.

Modified Examples

The present invention is not limited to the above embodiment.

For example, the posture detection unit 705 is not always necessary. In this case, the user may be considered to have assumed a specified posture after a predetermined time (for example, 3 seconds) has elapsed after an instruction to assume the specified posture, and the control unit 501 may execute the pulse transit time measurement and the blood pressure measurement in response to the elapse of the predetermined time from the instruction.

The posture instruction unit 704 does not have to specify a posture to be assumed. For example, the posture instruction unit 704 first notifies the user to assume a posture in which a height position of the measurement target site with respect to the heart varies each time a notification sound is emitted and may output the notification sound via the speaker 509 at an appropriate timing. An example of the posture to be assumed may be described in a user manual.

A blood pressure calculation expression for calculating the blood pressure value from the pulse transit time is not limited to the above expression (1). The blood pressure calculation expression may be, for example, the following expression.

$$SBP = B_1/PTT^2 + B_2/PTT + B_3 \times PTT + B_4$$

Here, $B_1$, $B_2$, $B_3$, and $B_4$ are parameters.

In the embodiment described above, the pulse wave sensor employs an impedance method in which a change in impedance resulting from a change in volume of the artery is detected. Also, the pulse wave sensor may adopt another measurement method such as a photoelectric method, a piezoelectric method, or a radio wave method. In an embodiment employing the photoelectric method, the pulse wave sensor includes: a light emitting element that radiates light toward the artery passing through a measurement target site; and a photodetector for detecting reflected light or transmitted light of the light, and the pulse wave sensor detects a change in light intensity resulting from a change in volume of the artery. In an embodiment employing the piezoelectric method, the pulse wave sensor includes a piezoelectric element provided on the belt to be in contact with the measurement target site and detects a change in pressure resulting from a change in volume of the artery. In an embodiment adopting the radio wave method, the pulse wave sensor includes: a transmitting element that transmits a radio wave toward the artery passing through the measurement target site; and a receiving element that receives a reflected wave of the radio wave and detects a phase shift between the transmitted wave and the reflected wave resulting from the change in volume of the artery.

In the embodiment described above, the pulse transit time is acquired using two pulse wave sensors. In another embodiment, the blood pressure measurement device may include: one pulse wave sensor and one electrocardiogram sensor and may acquire the pulse transit time, on the basis of a pulse wave signal acquired by the pulse wave sensor and an electrocardiogram representing an electrical activity of the heart of the user acquired by the electrocardiogram sensor.

The measurement target site is not limited to the upper arm and may be another site such as the wrist, thigh, or ankle.

The present invention is not limited to the embodiment described above as is and can be embodied by modifying the constituent elements within a range not departing from the gist of the invention in an implementation stage. Further, various inventions can be formed by appropriately combining a plurality of constituent elements disclosed in the embodiment described above. For example, some constituent elements may be omitted from the entire constituent elements shown in the embodiment. Furthermore, the constituent elements of different embodiments may be combined appropriately.

REFERENCE SIGNS LIST

10 Blood pressure measurement device
20 . . . Belt unit
21 . . . Belt
22 . . . Main body
23 . . . Strip
24 . . . Three-fold buckle
25 . . . First plate-shaped member
26 . . . Second plate-shaped member
27, 28 . . . Connecting rod
29 . . . fixing portion
30 . . . First blood pressure measurement unit
31 . . . Pulse transit time measurement unit
32 . . . Blood pressure value calculation unit
310 . . . Impedance measurement unit
310-1, 310-2 . . . Pulse wave sensor
311 to 316 . . . Electrodes
317 . . . Electrode group
318 . . . Energization and voltage detection circuit
40 . . . Second blood pressure measurement unit
41 . . . Pressing cuff
42 . . . Pressure sensor
43 . . . Pump
44 . . . Valve
45 . . . Oscillation circuit
46 . . . Pump drive circuit
50 . . . Posture instruction unit
60 . . . Calibration unit
501 . . . Control unit
502 . . . CPU
503 . . . RAM
504 . . . ROM
505 . . . Storage unit
506 . . . Display unit
507 . . . Operation unit
508 . . . Acceleration sensor
509 . . . Speaker
510 . . . Communication unit
511 . . . Battery
701 . . . Pulse transit time measurement control unit
702 . . . Blood pressure value calculation unit
703 . . . Blood pressure measurement control unit
704 . . . Posture instruction unit
705 . . . Posture detection unit
706 . . . Calibration unit
711 . . . Pulse transit time information storage unit
712 . . . First blood pressure value storage unit
713 . . . Second blood pressure value storage unit

The invention claimed is:

1. A blood pressure measurement device comprising:
a blood pressure measurement unit that includes a cuff and a pressure sensor detecting a pressure in the cuff and that is configured to measure blood pressure at a measurement target site of a measurement target subject, using the cuff and the pressure sensor;
a pulse transit time measurement unit including a first pulse wave sensor and a second pulse wave sensor, the pulse transit time measurement unit being configured to measure a pulse transit time at the measurement target site of the measurement target subject, using the first pulse wave sensor and the second pulse wave sensor; and
a processor configured to:
 instruct the measurement target subject to assume a plurality of postures in which height positions of the measurement target site with respect to a heart of the measurement target subject are different from each other;
 calibrate a relational expression representing a correlation between the pulse transit time and the blood pressure, on the basis of the blood pressure measured by the blood pressure measurement unit and the pulse transit time measured by the pulse transit time measurement unit, for each of the plurality of postures; and
 calculate a blood pressure value on the basis of measurement results of the pulse transit time and the calibrated relational expression.

2. The blood pressure measurement device according to claim 1, wherein the processor is configured to specify, as the plurality of postures, a posture in which the measurement target site is lower than the heart of the measurement target subject and a posture in which the measurement target site is higher than the heart.

3. The blood pressure measurement device according to claim 1, wherein the processor is configured to specify, as one of the plurality of postures, a posture in which the measurement target site is at a same height as the heart of the measurement target subject.

4. The blood pressure measurement device according to claim 1,
wherein processor is further configured to detect whether or not the measurement target subject has assumed a posture specified, and wherein the pulse transit time measurement unit and the blood pressure measurement unit respectively measure the pulse transit time and the blood pressure in a state in which the processor detects that the measurement target subject has assumed the posture specified.

5. The blood pressure measurement device according to claim 1, wherein the measurement target site is a wrist.

6. The blood pressure measurement device according to claim 2, wherein the processor further specifies, as one of the plurality of postures, a posture in which the measurement target site is at a same height as the heart of the measurement target subject.

7. The blood pressure measurement device according to claim 2,
wherein the processor is further configured to detect whether or not the measurement target subject has assumed a posture specified, and
wherein the pulse transit time measurement unit and the blood pressure measurement unit respectively measure the pulse transit time and the blood pressure in a state in which the processor detects that the measurement target subject has assumed the posture specified.

8. The blood pressure measurement device according to claim 3,
wherein the processor is further configured to detect whether or not the measurement target subject has assumed a posture specified, and
wherein the pulse transit time measurement unit and the blood pressure measurement unit respectively measure the pulse transit time and the blood pressure in a state in which the processor detects that the measurement target subject has assumed the posture specified.

9. The blood pressure measurement device according to claim 6,
wherein the processor is further configured to detect whether or not the measurement target subject has assumed a posture specified, and
wherein the pulse transit time measurement unit and the blood pressure measurement unit respectively measure the pulse transit time and the blood pressure in a state in which the processor detects that the measurement target subject has assumed the posture specified.

10. The blood pressure measurement device according to claim 2, wherein the measurement target site is a wrist.

11. The blood pressure measurement device according to claim 3, wherein the measurement target site is a wrist.

12. The blood pressure measurement device according to claim 4, wherein the measurement target site is a wrist.

13. The blood pressure measurement device according to claim 6, wherein the measurement target site is a wrist.

14. The blood pressure measurement device according to claim 7, wherein the measurement target site is a wrist.

15. The blood pressure measurement device according to claim 8, wherein the measurement target site is a wrist.

16. The blood pressure measurement device according to claim 9, wherein the measurement target site is a wrist.

* * * * *